United States Patent [19]

Marshall et al.

[11] Patent Number: 5,011,910

[45] Date of Patent: Apr. 30, 1991

[54] REAGENT AND METHOD FOR DETERMINING ACTIVITY OF RETROVIRAL PROTEASE

[75] Inventors: Garland R. Marshall; Mihaly V. Toth, both of Clayton, Mo.

[73] Assignee: Washington University, St. Louis, Mo.

[21] Appl. No.: 458,060

[22] Filed: Dec. 28, 1989

[51] Int. Cl.$^5$ .............................................. A61K 39/02
[52] U.S. Cl. .................................. 530/329; 530/327; 530/324; 435/23
[58] Field of Search ................... 530/327, 324; 514/11

[56] References Cited

U.S. PATENT DOCUMENTS 3,384,555 5/1968 Guilbault et al. ................ 195/103.5

OTHER PUBLICATIONS

Matayoshi et al., Novel Fluorogenic Substrates for Assaying Retroviral Proteases by Resonance Energy Transfer, Science, 1990, pp. 954–957.
Carmel and Yaron, Eur. J. Biochem. 87, 265–273 (1978).
Soler and Harris, Int. J. Peptide Protein Res. 32, 35–40 (1988).
Malfray and Brunier, Biochem. Biophys. Res. Commun. 143, 58–66 (1987).
Vencill et al., Biochemistry 24, 3149–3157 (1985).
Guilbault, Enzymatic Methods of Analysis, Pergamon Press, 1970, pp. 43–47.
Nashed et al., Biochem. Biophys. Res. Commun. 163, 1079–1085 (1989).
Hyland et al., Abstr. 2nd Int. Conf. Drugs Res. Immunologic and Infectious Disease, Aids New York Acad. Sci. I-20 (1989); Matayoshi, Ibid. I-26; Wang, Ibid. I-27.
Yaron et al., Anal. Biochem. 95, 228–235 (1979).

*Primary Examiner*—Lester L. Lee
*Assistant Examiner*—S. G. Marshall
*Attorney, Agent, or Firm*—Scott J. Meyer; James W. Williams, Jr.

[57] ABSTRACT

Novel fluorogenic substrates for retroviral protease, e.g. HIV protease, having the chemical structure X—Thr—Ile—Nle—Phe(Y)—Gln—Arg—NH$_2$ wherein X is a fluorogenic group and Y is an acceptor for the fluorogenic group, and their use in a fluorometric method for the determination of retroviral protease is disclosed.

2 Claims, 3 Drawing Sheets

REAGENT AND METHOD FOR DETERMINING ACTIVITY OF RETROVIRAL PROTEASE

BACKGROUND OF THE INVENTION

This invention relates to a reagent and method for determining the activity of retroviral protease, e.g. human immunodeficiency virus (HIV) protease. More particularly, the invention relates to novel fluorogenic substrates and a fluorometric assay for HIV protease and other retroviral proteases.

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names. It is the third known T-lymphocyte virus (HTLV-III) and has the capacity to replicate within cells of the immune system and thereby lead to a profound destruction of T4+ T-cells (or $CD4^{30}$ cells). See, e.g., Gallo et al., Science 224, 500–503 (1984), and Popovic et al., Ibid., 497–500 (1984). This retrovirus has been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [Ann. Virol. Inst. Pasteur 135 E, 119–134 (1984)], while HIV-2 was more recently isolated by Montagnier and his co-workers in 1986 [Nature 326, 662 (1987)]. As used herein HIV is meant to refer to these viruses in a generic sense.

A useful approach being investigated recently for potential use in the treatment of AIDS is the development of synthetic peptides as inhibitors of retroviral protease. Thus, it is known that retroviruses, including the human immunodeficiency virus (HIV), express their genetic content by directing the synthesis of a polyprotein by the host. This precursor is then processed by proteolysis to give essential viral enzymes and structural proteins. A virally encoded enzyme, the retroviral protease, is contained within the polyprotein and is responsible for the specific cleavages of the polyprotein yielding mature viral proteins.

Various novel peptide inhibitors of retroviral protease such as HIV protease are described in applicants' copending application Ser. No. 07/320,742, filed Mar. 8, 1989. Included among these are short peptides of about 4 to 8 amino acid residues derived from HIV cleavage sites such as, e.g. p24/p15, which have been modified to incorporate an internal $CH_2NH$ bond isostere. An illustrative example of such peptides is
Ac—Thr—Ile—Nle—ψ[$CH_2NH$]—Nle—Gln—Arg—$NH_2$.

HIV protease thus is a logical therapeutic target in the search for AIDS drugs. In order to facilitate the exploration of potential inhibitors of HIV protease and to optomize lead compounds, a convenient assay to kinetically characterize the inhibitor which allows for automation and high throughput would be desirable. Initial assays used in the characterization of HIV protease were based on HPLC separation of products and substrate at fixed time intervals. See Moore et al., Biochem. Biophys. Res. Commun. 159, 420–425 (1989); Darke et al., Ibid. 156, 297–303 (1988); Schneider and Kent, Cell 54, 363–368 (1988). The HPLC assay quickly became the rate-limiting step in the development of HIV protease inhibitors with desirable therapeutic properties. A continuous assay which allows for quantitative kinetic characterization of the interaction of the inhibitors with HIV protease would be preferable. The strategy of developing either a chromogenic or fluorogenic substrate is proposed by the present inventors based on their work characterizing short peptide substrates of known HIV protease cleavage sites. Toth et al., Proc. 11th Am. Peptide Symp., Rivier and Marshall, Eds., ESCOM, Leiden, In Press 1990. Fluorogenic substrates for hydrolytic enzymes have been widely used in biochemistry because of their high sensitivity. See, e.g., Guilbault, Enzymatic Methods of Analysis, Pergamon Press, 1970, pp. 43–47.

Recently, Nashed et al., Biochem. Biophys. Res. Commun. 163, 1079–1085 (1989), and Hyland et al., Abstr. 2nd Int. Conf. Drugs Res. Immunologic and Infectious Disease. AIDS. New York Acad. Sci., I-20 (1989), have reported a spectrophotometric assay based on cleaved chromogenic substrates containing p—$NO_2$—Phe at position P1. In these cases, the substances were an octapeptide, a nonapeptide, and a decapeptide. A high-throughput, radiometric assay for screening for HIV protease inhibitors, which is not continuous, has also been reported by Hyland et al., supra.

BRIEF DESCRIPTION OF THE INVENTION

In accordance with the present invention novel fluorogenic substrates and a fluorometric assay for retroviral protease, e.g. HIV protease, utilizing these substrates are provided.

The preferred novel substrates are based on the hexapeptide, Ac—Thr—Ile—Nle—Nle—Gln—Arg—$NH_2$, derived from the p24/p15 cleavage site of HIV protease. This hexapeptide is modified whereby a fluorogenic group, e.g. 2-aminobenzoic acid (Abz), is preferably incorporated in place of the acetyl group (Ac) as the donor, and an acceptor of the fluorogenic group, e.g. p-nitrophenylalanine (p—$NO_2$—Phe), is preferably incorporated at the P1' position as acceptor to provide the novel intramolecularly quenched fluorogenic substrate, X—Thr—Ile—Nle—Phe(Y)—Gln—Arg—$NH_2$, wherein X is the fluorogenic group and Y is the acceptor for the fluorogenic group. A preferred fluorogenic substrate thus is Abz—Thr—Ile—Nle—Phe(p—$NO_2$)—Gln—Arg—$NH_2$. For convenience, this novel substrate is also designated herein as Abz—NF*—6.

The novel fluorometric assay is a method for the determination of retroviral protease, e.g. HIV protease, which comprises: placing a known amount of the novel fluorogenic substrate in a fluorescence cell of a spectrophotofluorometer, incubating with a known amount of the retroviral protease at 37° C., measuring the change in fluorescence with time and determining the molar velocity of the retroviral protease by comparing against a standard curve which relates changes in fluorescent intensity to changes in concentration of product.

It will be appreciated that various modifications can be made to the aforesaid preferred fluorogenic substrates to provide substantially similar useful results in the fluorometric assay for retroviral protease. Thus, in the assay for HIV protease, X can be any fluorogenic group (anthracene, aminobenzoyl, indole, aminoethylnaphthyl, and the like) which can be modified and attached to the N-terminal amino function such as Abz, dansyl (5-dimethylamino-naphthalene-1-sulfonyl), nicotinic acid, 4-guanidino-benzoic acid, and derivatives thereof, e.g. N-methyl-Abz, 4-chloro-Abz, 5-chloro-Abz, 6-chloro-Abz, 3,5-dibromo-Abz; derivatives of nicotinic acid such as 6-amino-, 2-amino-, 2-chloronicotinic acid, and niflumic acid; derivatives of 4-guanidinobenzoic acid; derivatives of dansyl; and the like derivatives.

Y can be any amino acid derivative which has a quenching aromatic group which absorbs the fluorescence energy of the fluorogenic donor X and reduces the fluorescence emission when X and Y are covalently held in close proximity. Examples are Trp, Tyr, Phe(p—$NO_2$), Phe(m—$NO_2$), and halogenated derivatives thereof.

Besides variations in the fluorescence donor and acceptor groups, X and Y, the amino acids in the substrate sequences can be varied to optimize the affinity and kinetic properties for the particular retroviral protease under consideration.

In the case of HIV protease, position three (Nle) can be replaced by Leu, Val, Ile, Phe, Tyr, Cha and other hydrophobic residues. Position 2 (Ile) can similarly be varied with other hydrophobic residues. Position one (Thr) can be replaced with hydrophilic residues such as Ser, Glu, Arg, Lys, and the like. Position 5 (Gln) can be replaced with a variety of hydrophobic and hydrophilic residues. Position 6 (Arg) can be replaced with hydrophilic residues, Lys, HArg, Glu, Asp, and the like.

Alternatively, positions of donor and acceptor groups can be interchanged with an acceptor, or quenching group in position X and a donor group incorporated into an amino acid in position Y. For example, p-nitrobenzoic acid can be used for X and Phe(m—$NH_2$) for Y.

The acceptor group Y can be located at other positions in the C-terminal section of the cleaved product such as replacing the Gln in position 5 or the Arg in position 6. In those cases, position four would be occupied by hydrophobic residues such as Leu, Val, Ile, Phe, Cha, Tyr and Nle. The C-terminal amide can be replaced by the acceptor group such as nitrobenzylamine as well. This would not be as desirable as the increased distance between the donor and acceptor in the substrate would increase the background fluorescence and make the difference upon cleavage smaller. This may be necessary, however, in order to accomodate particular substrate requirements of a given retroviral protease.

DETAILED DESCRIPTION OF THE INVENTION

Figure 1:
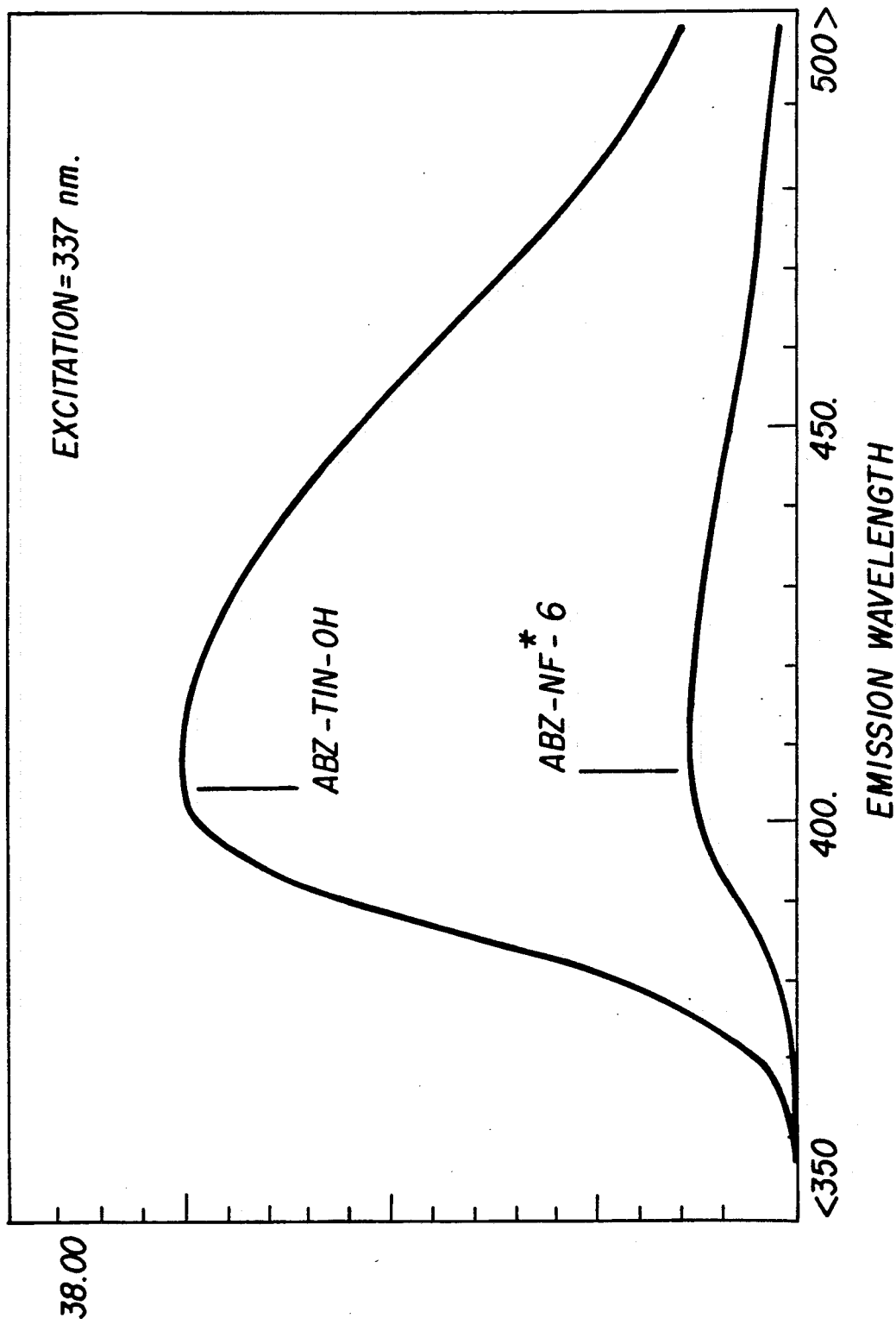

While the specification concludes with claims particularly pointing out and distinctly claiming the subject matter regarded as forming the present invention, it is believed that the invention will be better understood from the following detailed description of preferred embodiments of the invention taken in conjunction with the appended drawings, in which, briefly:

FIG. 1 is a graphical representation which shows emission spectra (excitation wavelength=337 nm) of 0.1 mM solutions of an illustrative novel substrate of the invention, Abz—Thr—Ile—Nle—Phe(p—$NO_2$)—Gln—Arg—$NH_2$(ABZ—NF*—6) and product, Abz—Thr—Ile—Nle—OH(ABZ—TIN—OH), demonstrating quenched fluorescence in substrate due to proximity of donor (ABZ) and acceptor (Phe(p—$NO_2$)) chromophores. Fluorescence magnitude is plotted versus emission wavelength.

Figure 2:
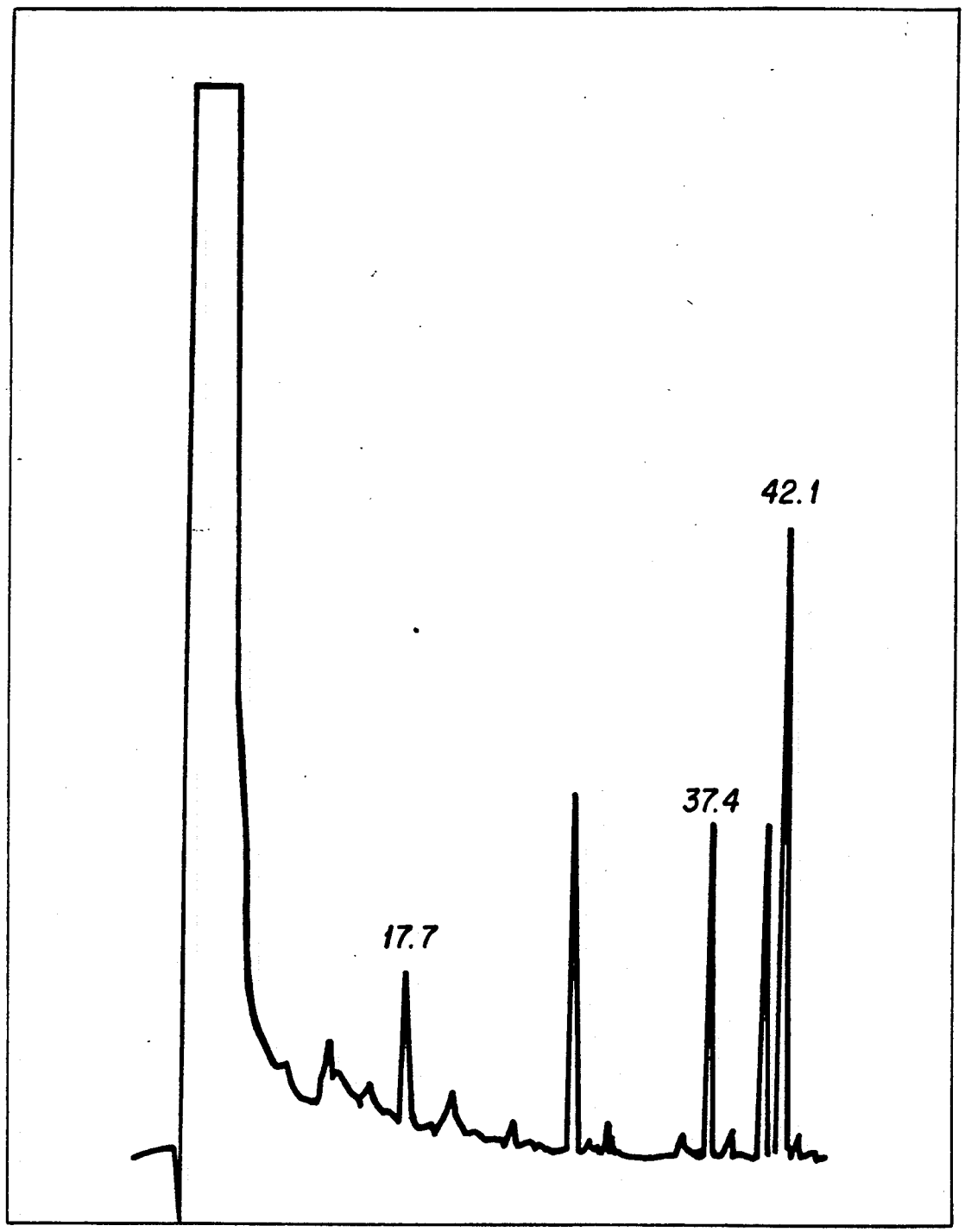

FIG. 2 is a graphical representation which shows the HPLC profile of elution pattern of Abz—Thr—Ile—Nle—Phe(p—$NO_2$)—Gln—Arg—$NH_2$(ABZ—NF*—6), elution time=42.1 min, and products, Abz—Thr—Ile—Nle—OH (elution time=37.4 min) and H—Phe(p—$NO_2$)—Gln—Arg—$NH_2$ (elution time=17.7 min). Other peaks are due to buffer components. UV absorbtion is plotted versus time.

Figure 3:
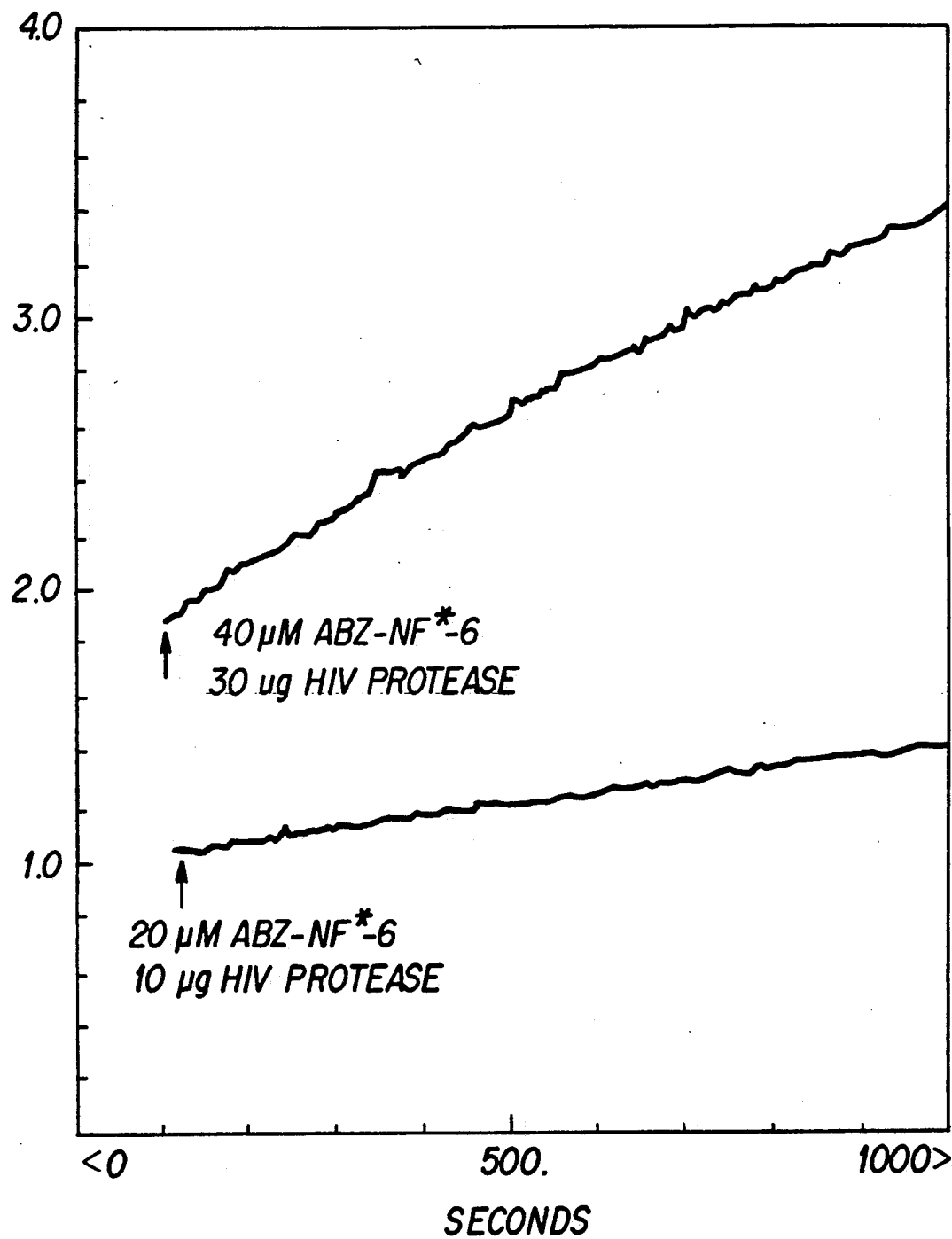

FIG. 3 is a graphical representation which shows the fluorescence emission increase as function of time demonstrating linear portion of assay under conditions used. Initial kinetics were monitored on the SLM 8000 C fluorometer at 25° with magnetic stirring at optimal conditions (excitation=337 nm and emission=410 nm). Fluorescence is plotted versus time.

The preferred novel fluorogenic substrates of this invention and their analogs can be made by known solution and solid phase peptide synthesis methods but modified to incorporate the acceptor residue, e.g. Phe(p—$NO_2$), in the P1' position, and the fluorogenic group, e.g. 2-aminobenzoic acid (Abz), at the N-terminal position and amide at the C-terminus. The preferred peptide syntheses method follows conventional Merrifield solid-phase procedure [*J. Amer. Chem. Soc.* 85, 2149-54 (1963); *Science* 150, 178-85 (1965)]modified by the procedure of Tam et al., *J. Amer. Chem. Soc.* 105, 6442-6445 (1983).

In order to illustrate specific preferred embodiments of the invention in greater detail, the following exemplary laboratory preparative work was carried out. It should be understood that the invention is not limited to these specific examples.

EXAMPLES

Materials and Methods

Solid phase synthesis of HIV protease substrates. Acetyl hexapeptide amides were prepared by conventional solid phase peptide synthesis using p-methylbenzhydrylamine polymer. For each synthesis, 0.5 grams of polymer was used (0.5 mmole). The following synthetic protocol was used for incorporation of the Boc-amino acids:

| Deprotection: | |
|---|---|
| 50% trifluoroacetic acid/$CH_2Cl_2$ 5 min and 25 min | |
| $CH_2Cl_2$ | 2 × 1 min |
| Isopropanol | 2 × 1 min |
| $CH_2Cl_2$ | 2 × 1 min |
| Neutralization: | |
| 10% diisopropylethylamine/$CH_2Cl_2$ 3 min and 5 min | |
| $CH_2Cl_2$ | 2 × 1 min |
| DMF | 2 × 1 min |

Coupling: 4 equivalent of Boc-amino acid and 4 equivalents of diisopropylcarbodiimide in the presence of 4 equivalents of hydroxybenzotriazole in DMF for 2 hours. Coupling in DMF was repeated if the Kaiser test were positive. Completed peptides were cleaved by the HF/anisole 9:1 procedure of Tam et al., *J. Am. Chem. Soc.* 105, 6442-6445 (1983). Crude peptides were dissolved in 20% acetic acid and lyophilized. They were purified by reversed-phase HPLC on a $C_{18}$ semipreparative column using a 0.1% TFA and acetonitrile gradient. Their identity was confirmed by high-resolution mass spectrometry, NMR and amino acid analyses.

HPLC Assay. The HPLC HIV protease assay was conducted using either synthetic HIV protease [Schneider and Kent, *Cell* 54, 363-368 (1988)] in which the two Cys residues ($Cys^{67}$, $Cys^{95}$) were replaced by the isosteric α-aminobutyric acid to eliminate the complications of free sulfhydryl groups, of cloned material expressed in *E. coli*. In all cases examined, the cleavage patterns and inhibition results were identical. Synthetic HPLC-purified protease (0.05 mg/ml) was dissolved in assay buffer (20 mM phosphate, 20% glycerol, 0.1% CHAPS, pH 6.4). 20 μl of 0.1 mM substrate was mixed with 20 μl assay buffer and 10 μl of HIV protease stock were added and then incubated at 25° for the desired time. The reaction was stopped by the addition of 50 μl of 10% TFA. The sample was applied to a $C_{18}$ HPLC column developed with 0.05% TFA for 5 min followed by a gradient of 0-40% acetonitrile in 40 min. For inhibitor studies, 10 μl of the protease solution was preincubated at 25° for 10 min with the 20 μl of 0.1 mM inhibitor (dissolved in DMSO and diluted to 0.1 mM with assay buffer). Then 20 μl of test substrate, acetyl—Thr—Ile—Met—Met—Gln—Arg—$NH_2$ or Abz—NF*—6, was added in order to determine inhibition of cleavage. Reactions were stopped and cleavage rates were monitored by HPLC as above. In order to confirm the cleavage pattern of Abz—Thr—Ile—Nle—Phe(p—$NO_2$)—Gln—Arg—$NH_2$, cleavage was allowed to finish as judged by HPLC and the two product peaks were isolated by HPLC. Incubation with either synthetic HIV protease or enzyme expressed and purified from *E. coli* gave the same HPLC pattern (FIG. 2). Retention time of the substrate was 41.1 min, while Abz—Thr—Ile—Nle was 37.4 min and Phe(p—$NO_2$)—Gln—Arg—$NH_2$ was 17.7 min. Identity of the product peptides was confirmed by FABMS and amino acid analysis.

Fluorescence Spectra. The excitation and emission spectra were measured on a SLM 8000 C spectrometer. Both the substrate, Abz—NF*—6, and the N-terminal product, Abz—Thr—Ile—Nle—OH, show absorption maxima at 337 nm and broad emission maxima between 390-440 nm. The comparison between substrate and product at the same concentration shows dramatically the increase of ten fold in excitation and 6 fold in emission upon enzymatic hydrolysis. Initial kinetics were monitored at 25° with magnetic stirring at optimal conditions (excitation =337 nm and emission=410 nm).

UV Spectra. The absorbtion spectra of the substrate, Abz—NF*—6, and the N-terminal product, Abz—Thr—Ile—Nle—OH, were recorded on a Bechman DU-8 spectrophotometer. The substrate shows maxima at 328 nm and 254 nm while the cleavage product has maxima at 318 nm and 252 nm.

Fluorescence Assay. Fluorescence measurements on 96-well ELISA plates were made with the Titertek Fluoroskan II, version 3.1. An excitation filter of 355 nm and an emission filter of 430 nm was used. Ten μl of a stock solution (0.1 mg/ml) of HIV protease was incubated with five different concentrations of Abz—NF*—6 in a final volume of 100 μl at 37° C. with the increase in fluorescence monitored in each well every five minutes. A stock solution of 1 mM Abz—NF*—6 in DMSO was used. A standard curve relating changes in fluorescent intensity to changes in concentration of product was used to convert fluorescence changes into molar velocities. In order to predetermine the concentration range for $K_i$ determination of inhibitors, it was found convenient to do a preliminary assay by HPLC. Twenty μl of 0.1 mM inhibitor in assay buffer (pH 6.4) and 10 μl of HIV protease (stock solution of 0.05 mg/ml) were preincubated for 5-10 min at 25° C. Twenty μl of 0.1 mM Abz—NF*—6 was added and the reaction continued for 1 hour. Sixty μl of 10% TFA was added to stop the reaction and the amount of cleavage determined by HPLC. In the absence of inhibition, complete cleavage occurs. By the amount of substrate remaining, an estimated $K_i$ allows appropriate choice of concentration ranges for the inhibitor for the fluorescence assay.

Results

Six peptides were thus prepared as potential chromogenic substrates with the following sequences:
H—Ser—Phe—Asn—Phe(p—$NO_2$)—Pro—Gln—Val—Thr—OH
H—Arg—Lys—Ile—Leu—Phe(p—$NO_2$)—Leu—Asp—Gly—OH
H—Thr—Leu—Asn—Phe(p—$NO_2$)—Pro—Ile—Ser—Pro—OH
Ac—Leu—Asn—Phe(m—$NO_2$)—Pro—Ile—Ser—$NH_2$
Ac—Thr—Ile—Phe(p—$NO_2$)—Nle—Gln—Arg—$NH_2$
Ac—Thr—Ile—Nle—Phe(p—$NO_2$)—Gln—Arg—$NH_2$.

Of the six peptides, only the last with the Phe(p—$NO_2$) residue in the P1' position showed cleavage under the desired conditions of HPLC assay and with incubation times of one hour. Hyland et al., supra., have reported a chromogenic octapeptide substrate, Ac—Arg—Lys—Ile—Leu—Phe(p—$NO_2$)—Leu—Asp—Gly—$NH_2$, which is somewhat analogous to one prepared above, but with blocked amino and carboxyl terminals. Nashad et al., supra., have reported two chromogenic peptide substrates, Ac—Lys—Ala—Ser—Gln—Phe(p—$NO_2$)—Pro—Val—val—$NH_2$ and H—Thr—Phe—Gln—Ala—Phe(p—$NO_2$)—Pro—Leu—Arg—Ala—OH, which can form the basis of a spectrophotometric assay. In these three cases, however, the hydrolysis occurs to leave the chromogenic residue at the C-terminus, resulting in greater spectral changes. Because of the small spectral changes seen with the chromogenic residue at the N-terminus, the novel fluorogenic substrate defined herein was developed to provide a novel fluorometric assay.

Modification of the hexapeptide substrate, Ac—Thr—Ile—Nle—Phe(p—$NO_2$)—Gln—Arg—$NH_2$, with the acceptor residue in the C-terminal product required the addition of a donor fluorescent group to the N-terminal product. Replacing the acetyl group with 2-aminobenzoic acid (Abz) resulting in the novel fluorogenic peptide, Abz—Thr—Ile—Nle—Phe(p—$NO_2$)—Gln—Arg—$NH_2$, gave the same combination of donor and acceptor used by Carmel and Yaron, *Eur. J. Biochem.* 87, 265-273 (1978), in their substrate for angiotensin converting enzyme. Since those authors had shown that quenching efficiency depends on the proximity of the donor and acceptor chromophores, an analog with the Abz group at position P3, Abz—Ile—Nle—Phe(p—$NO_2$)—Gln—Arg—$NH_2$ was synthesized by the present inventors, but the cleavage efficiency was dramatically reduced. The above novel hexapeptide substrate of the invention, also referred to as Abz—NF*—6, shows a small amount of fluorescent background due to incomplete quenching of the fluorophore, but an approximate 6-fold increase in fluorescence upon hydrolysis with a broad maximum between 390 and 440 nm as seen in FIG. 1. A variety of other fluorescent groups can be incorporated in the P4 position consistent with its surface location as seen in the X-ray crystal structure [Miller et al., *Science* 246, 1149-1152 (1989)] of the complex of synthetic HIV protease with MVT-101, an inhibitor of similar structure, Ac—Thr—Ile—Nle—$\psi$[CH$_2$NH]—Nle—Gln—Arg—NH$_2$.

Kinetic measurements of the cleavage of Abz—NF*—6 by synthetic HIV protease showed typical Michaelis-Menten behaviour with linear kinetics over the twenty minutes of reaction when less than 15% of the substrate is cleaved by the enzyme (FIG. 3). A Lineweaver-Burk plot of the velocities calculated from the linear phase of the reactions gave a $K_m$=110 mM. $V_{max}$ was calculated to be 3.45 mM-mil$^{-1}$ with a $K_{cat}$=2.9 sec$^{-1}$. The chromogenic substrates of Nashed et al., *Biochem. Biophys. Res. Commun.* 163, 1079-1085 (1989), had $K_m$'s estimated to be greater than 450 mM. The ratio $K_{cat}/K_m$ for Abz—NF*—6 with synthetic HIV protease is 26,364 M$^{-1}$s$^{-1}$, while the ratio for the nonapeptide chromogenic substrate of Nashed et al., supra., was estimated to be 23,000 M$^{-1}$s$^{-1}$ using purified HIV protease expressed in *E. coli.*

Utilizing the novel fluorogenic substrate of the present invention, Abz—NF*—6, a screening procedure for potential HIV protease inhibitors was established which allowed the determination of inhibitor affinity. Eight wells allowed the determination of the effect of four different concentrations of inhibitor on two substrate concentrations which was minimally sufficient to calculate a $K_i$ value based on a Dixon plot (1/v vs. inhibitor concentration). Fluorescence was measured every two minutes for 20 minutes. Thus, it is feasible to determine the affinity of 12 inhibitors in twenty minutes. This is to be contrasted with the HPLC analysis which requires about 30 separate HPLC runs, each of which takes approximately one hour, for the determination of one $K_i$. Under routine conditions, however, one would likely run determinations in duplicate and include a inhibitor standard which would reduce the number of $K_i$ determinations to 15 per hours.

Amino acids are shown herein by standard three letter abbreviations as follows:

| Abbreviated Designation | Amino Acid |
|---|---|
| Ala | Alanine |
| Cys | Cysteine |
| Asp | Aspartic acid |
| Glu | Glutamic acid |
| Phe | Phenylalanine |
| Gly | Glycine |
| His | Histidine |
| Ile | Isoleucine |
| Lys | Lysine |
| Leu | Leucine |
| Met | Methionine |
| Asn | Asparagine |
| Pro | Proline |
| Gln | Glutamine |
| Arg | Arginine |
| Ser | Serine |
| Thr | Threonine |
| Val | Valine |
| Trp | Tryptophan |
| Tyr | Tyrosine |

Other standard abbreviations used herein are:
Nle = norleucine,
Abz = 2-aminobenzoic acid,
Ac = acetyl,
Cha = cyclohexylalanine,
TFA = trifluoroacetic acid,
DMF = dimethylformamide,
DMSO = dimethylsulfoxide,
CHAPS = 3-[(3-chloramidopropyl)-dimethylammonio]-1-propanesulfonate, and
FABMS = fluroescent antibody mass spectrometry.

Various other examples will be apparent to the person skilled in the art after reading the present disclosure without departing from the spirit and scope of the invention. It is intended that all such other examples be included within the scope of the appended claims.

What is claimed:

1. A fluorogenic substrate for retroviral protease having the chemical structure
X—Thr—Ile—Nle—Phe(Y)—Gln—Arg—NH$_2$
wherein X is a fluorogenic group which is capable of being attached to said Thr and conferring fluorescence on said substrate and Y is an acceptor which is capable of providing intramolecular quenching of said fluorescence.

2. A fluorogenic substrate for retroviral protease having the chemical structure
Abz—Thr—Ile—Nle—Phe(p—NO$_2$)—Gln—Arg—NH$_2$.

* * * * *